US006394988B1

(12) United States Patent
Hashimoto (10) Patent No.: US 6,394,988 B1
(45) Date of Patent: May 28, 2002

(54) ADJUSTABLE CONSTRUCTION OF DIAPER CUP FOR DISCHARGE DISPOSING APPARATUS

(75) Inventor: Takeo Hashimoto, Tokyo (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 09/497,486

(22) Filed: Feb. 4, 2000

(30) Foreign Application Priority Data

Feb. 16, 1999 (JP) ............................................ 11-036648

(51) Int. Cl.⁷ .............................. A61F 5/44; A61F 5/442
(52) U.S. Cl. ....................................... 604/355; 604/327
(58) Field of Search .................................. 604/304, 305, 604/313, 316, 327, 347, 348, 355, 361, 393, 289, 290; 4/666; 2/11, 14, 174

(56) References Cited

U.S. PATENT DOCUMENTS

| 2,749,558 A | * | 6/1956 | Lent et al. | |
| 3,626,941 A | * | 12/1971 | Webb | 128/283 |
| 3,751,727 A | * | 8/1973 | Shepard et al. | 2/2.1 A |
| 4,200,102 A | * | 4/1980 | Duhamel et al. | 128/286 |
| 4,281,655 A | * | 8/1981 | Terauchi | 128/278 |
| 4,631,061 A | * | 12/1986 | Martin | 604/318 |
| 4,747,166 A | * | 5/1988 | Kuntz | 4/144 |
| 4,791,686 A | * | 12/1988 | Taniguchi et al. | 4/448 |
| 4,834,110 A | * | 5/1989 | Richard | 128/760 |
| 4,886,508 A | * | 12/1989 | Washington | 604/327 |
| 4,982,462 A | * | 1/1991 | Wada | 4/546 |
| 5,004,463 A | * | 4/1991 | Nigay | 604/329 |
| 5,342,583 A | * | 8/1994 | Son | 422/107 |
| 5,678,564 A | * | 10/1997 | Lawrence et al. | 128/761 |
| 5,681,297 A | | 10/1997 | Hashimoto et al. | |
| 5,911,222 A | * | 6/1999 | Lawrence et al. | 128/761 |
| 6,110,159 A | * | 8/2000 | Tsujita et al. | 604/387 |

FOREIGN PATENT DOCUMENTS

| GB | 2 050 838 A | * | 1/1981 | ............ A61M/1/00 |
| JP | 4-364841 | | 12/1992 | |
| WO | WO 93/07839 | * | 4/1993 | ............ A61F/5/451 |

* cited by examiner

Primary Examiner—John G. Weiss
Assistant Examiner—Michael Bogart
(74) Attorney, Agent, or Firm—Ronald P. Kananen, Esq.; Rader, Fisher & Grauer, PLLC (57) ABSTRACT

A discharge disposing apparatus is provided with a diaper cup body 2 enveloping the waist and hips of a human body, a cleaning water feeding hose connected to the diaper cup body 2 for feeding water into the inside of the diaper cup body, and a filth sucking hose connected to the diaper cup body 2 for sucking the cleaning water and the filth from within the inside of the diaper cup body. The diaper cup body 2 is composed of a base body 2x provided with the cleaning water feeding hose 2p and the filth sucking hose 2n, a caterpillar-like joint 2a rotatably coupled with the base body 2x, and a front cover 2b rotatably coupled with the caterpillar-like joint 2a. The caterpillar-like joint 2a is connected with a plurality of joint pieces 2a1, 2a2, 2a3, 2a4, and 2a5. The diaper of the present invention provides a discharge disposing apparatus in which the exchange operation is made easily without any leakage of water, and the diaper cup body 2 is adjustable to fit human bodies of different sizes.

12 Claims, 7 Drawing Sheets

ADJUSTABLE CONSTRUCTION OF DIAPER CUP FOR DISCHARGE DISPOSING APPARATUS

BACKGROUND OF THE INVENTION

1. Field of the Invention

The present invention relates to a discharge disposing apparatus to be applied as a diaper to a patient unable to walk, a bedridden old person in a hospital, and the like. More particularly, the present invention relates to a discharge disposing apparatus that automatically disposes of filth and cleans the soiled private parts of a patient who discharges the filth.

2. Description of the Prior Art

A conventional discharge disposing apparatus is disclosed, for example, in Japanese Patent Publication Laid-Open No. 4-364841. In this conventional apparatus, the waist and hips of a human body are enveloped by a diaper cup body.

The diaper cup body of the conventional discharge disposing apparatus is made of resilient plastic material for the sake of exchanging the cover. However, it is difficult to suitably fit the diaper cup body to persons who wear the diaper cup body because such persons have different physiques and sizes of the waist and hips. Thus, a leakage of cleaning water is often caused by a poor fitting diaper cup body.

SUMMARY OF THE INVENTION

An object of the present invention is to present a discharge disposing apparatus that solves the problems with the conventional discharge disposing apparatus mentioned above.

More specifically, an object of the present invention is to provide a discharge disposing apparatus having a diaper cover that can be easily exchanged without any leakage of water.

Additional objects, advantages and novel features of the invention will be set forth in part in the description that follows, and in part will become apparent to those skilled in the art upon examination of the following or may be learned by practice of the invention. The objects and advantages of the invention may be realized and attained by means of the instrumentalities and combinations particularly pointed out in the appended claims.

According to a broad aspect of the present invention, a discharge disposing apparatus is provided comprising: a diaper cup body enveloping the waist and hips of a human body, a cleaning water feeding hose connected to the diaper cup body for feeding water into the inside of the diaper cup body, and a filth sucking hose connected to the diaper cup body for sucking the cleaning water and the filth within the inside of the diaper cup body. The diaper cup body is composed of a base body provided with the cleaning water feeding hose and the filth sucking hose, a caterpillar-like joint rotatably coupled with the base body, and a front cover rotatably coupled with the caterpillar-like joint. The caterpillar-like joint is connected with a plurality of joint pieces, and the size of the diaper cup body can be adjustable by increasing or decreasing the number of the joint pieces.

According to other aspects of the invention, the joint pieces are integrally formed with curve sections, tongue pieces are formed at both sides of the curve sections, and joint holes are provided at the front and the rear portions of each of the tongue pieces. The joint pieces are formed with thin sections at the periphery of the joint holes mounted on the tongue pieces. The joint holes of the joint pieces are connected by pivot members with each other. The pivot members are passed through the joint holes of the joint pieces and fastening holes mounted on a water proof cloth to fasten the water proof cloth to the joint pieces for covering the caterpillar-like joint with the water proof cloth.

The pivot members are composed of a rod member and a snap member, the rod member is formed with a head section at one end thereof and a projection section at the other end thereof to form a cylinder section, and the snap member is formed with a head section at one end thereof and a projection section at the other end thereof to form a snap hole section.

BRIEF DESCRIPTION OF THE DRAWINGS

The present invention will become more clearly appreciated as the disclosure of the invention is made with reference to the accompanying drawings. In the drawings.

DETAILED DESCRIPTION OF THE PREFERRED EMBODIMENTS

A discharge disposing apparatus according to the preferred embodiment of the present invention will now be described in detail with reference to FIGS. 1 to 9 of the accompanying drawings.

Figure 1:
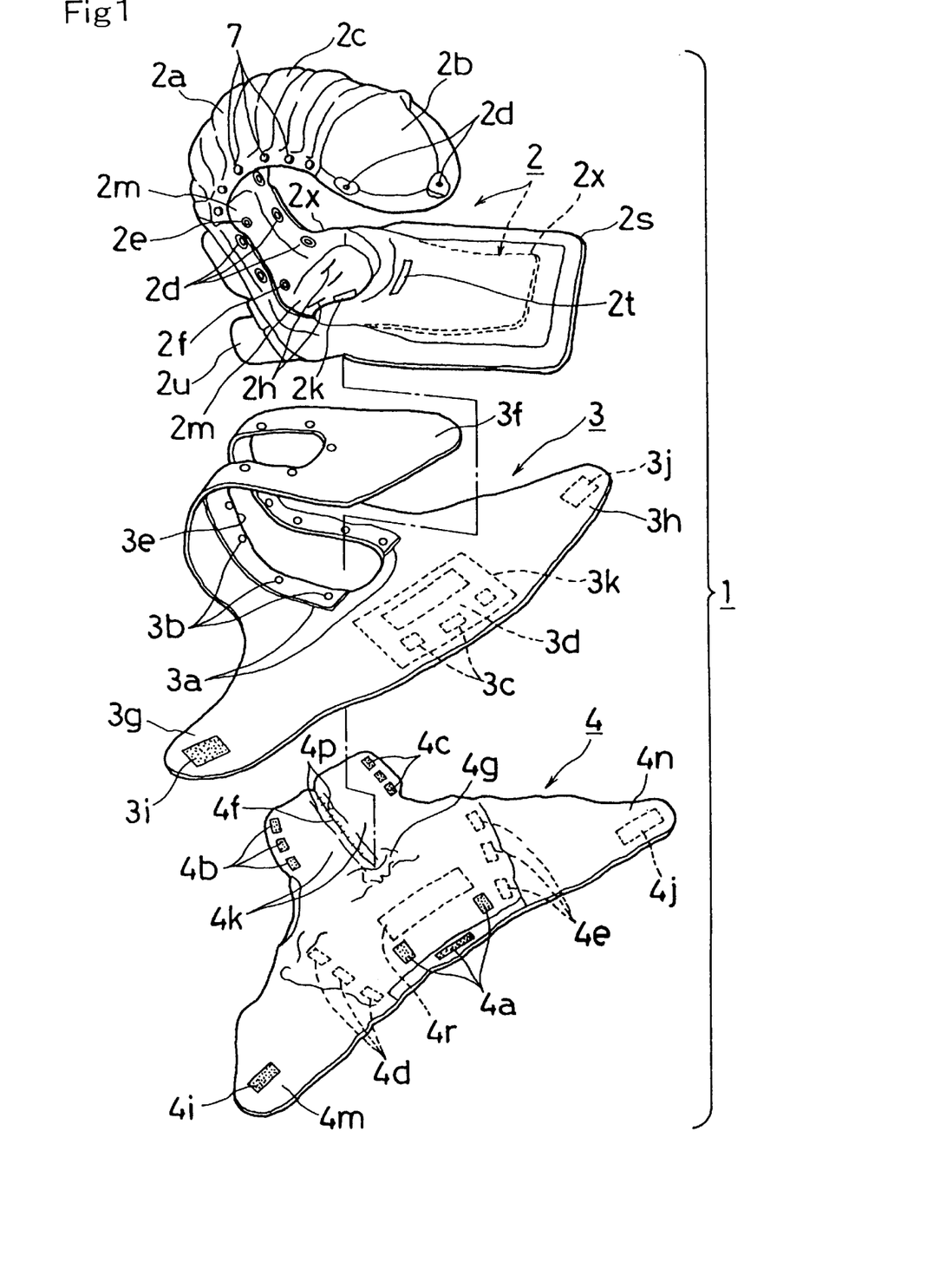
FIG. 1 is an exploded perspective view showing a preferred embodiment of the present invention.
Figure 4:
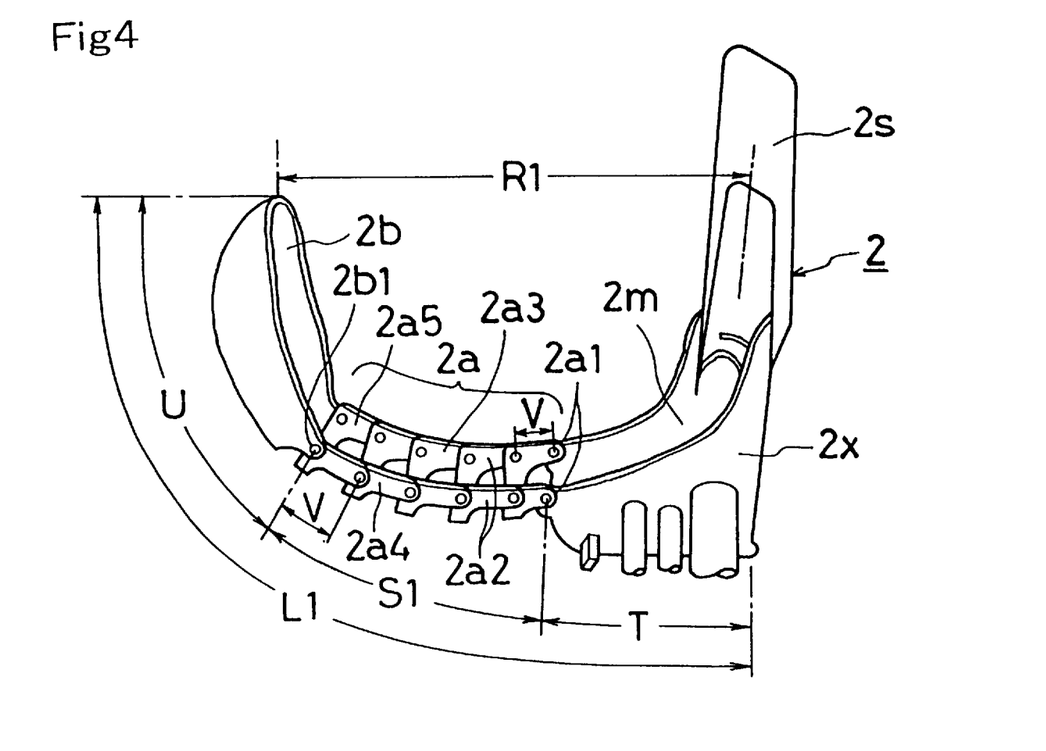
FIG. 4 is a perspective view showing an L-size diaper cup body in which a water proof cloth is removed in the preferred embodiment of the present invention.

Referring now to FIG. 1, a diaper cup unit 1 is shown composed of a diaper cup body 2, a spare diaper 3, and a diaper cover 4. As shown in FIG. 4, the diaper cup body 2 is formed with resin material having an approximately U-letter shape for enveloping the waist and hips of a human body. The diaper cup body 2 is formed with a base body 2x, a caterpillar-like joint 2a connected to the base body 2x, and a front cover 2b connected to the caterpillar-like joint 2a.

Figure 2:
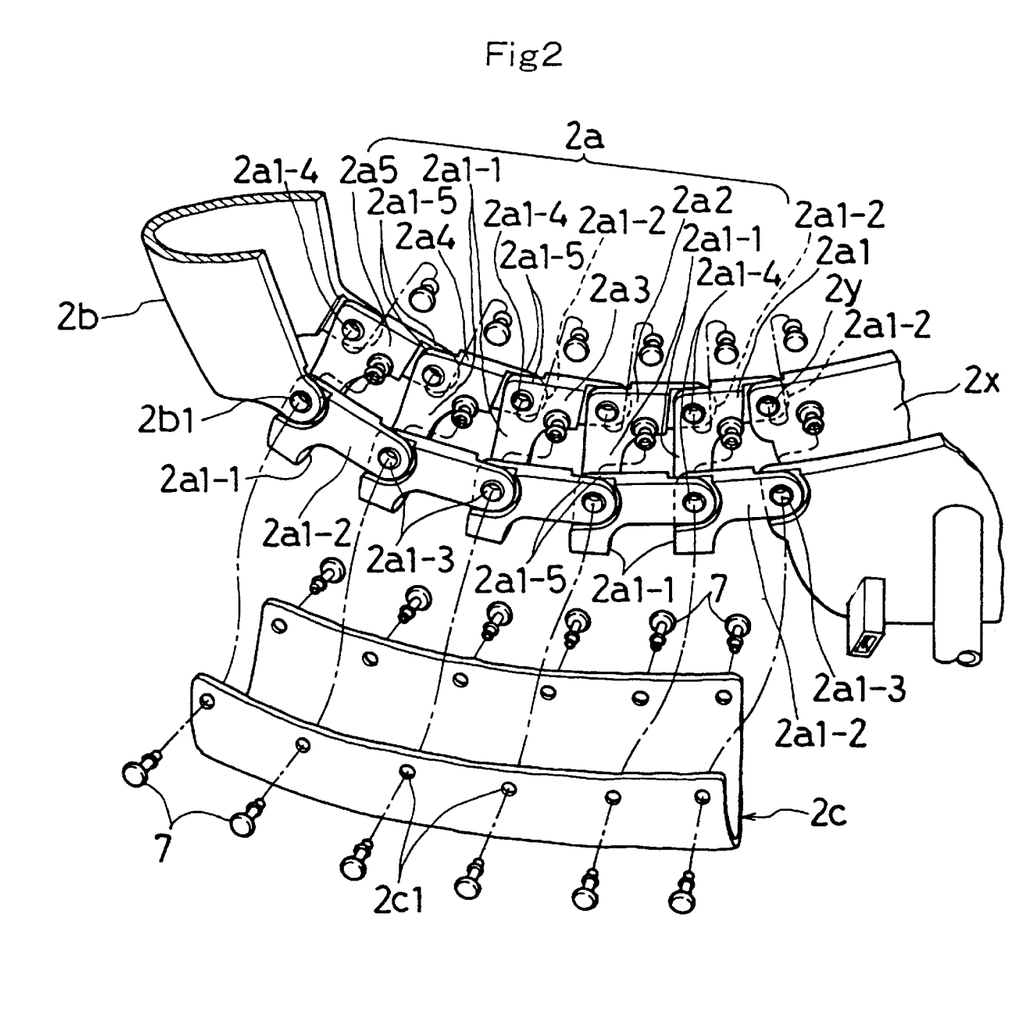
FIG. 2 is an enlarged exploded perspective view showing the main portion of the caterpillar-like joint of a diaper cup body in the preferred embodiment of the present invention.
Figure 3:
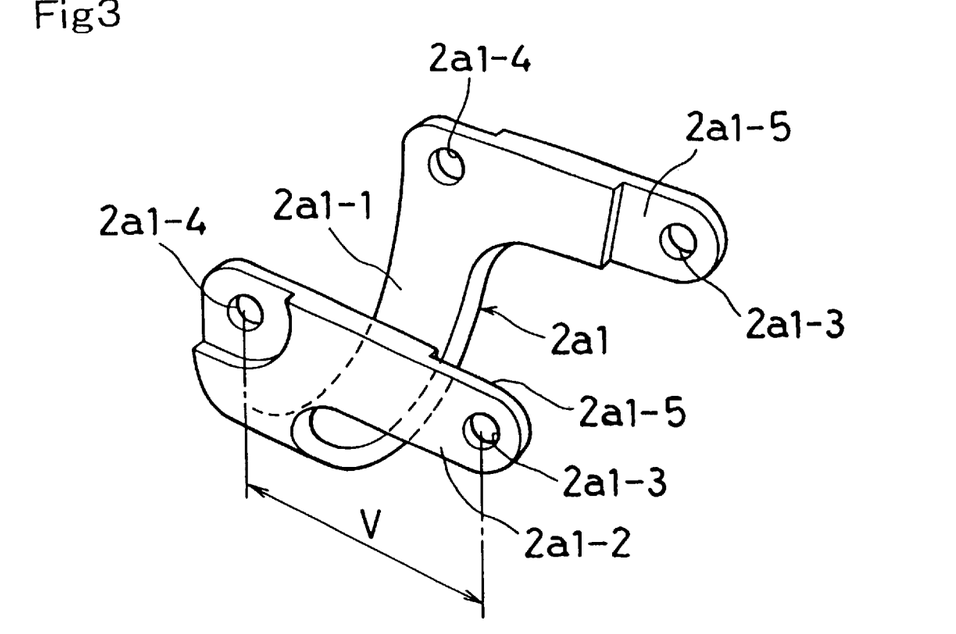
FIG. 3 is an enlarged exploded perspective view showing a joint piece used in the preferred embodiment of the present invention.

The base body 2x is formed with, for example, urethane hard resin material having an approximately J-letter shape for covering the central portion of the waist and hips. The base body 2x is integrally formed with a cavity 2m at the inner side thereof, a waist board 2s at the upper end thereof, and a connecting section $2u$ for connection with hoses and an electric connector at the lower surface thereof. The base body $2x$ is rotatably coupled with the caterpillar-like joint $2a$ at the lower end thereof. As shown in FIGS. 1 and 2, the base body $2x$ is provided with hooks $2d$, a nozzle $2e$ for cleaning the private parts, a nozzle $2f$ for cleaning the anus, a nozzle $2g$ for cleaning the cup, a sensor $2h$ for sensing feces, an outlet $2i$ for exhausting warm wind, an auxiliary outlet $2j$, and a sensor $2k$ for sensing urine.

As shown in FIG. 2, the caterpillar-like joint $2a$ is formed with plural joint pieces $2a1$, $2a2$, $2a3$, $2a4$ and $2a5$ each of which has the same formation and is connected with each other for allowing flexible motion of the caterpillar-like joint. The joint $2a$ is covered with a water proof cloth $2c$ maintaining the flexibility of the caterpillar-like joint $2a$ and further avoiding any leakage of cleaning water.

As shown in FIG. 2, the joint pieces $2a1$, $2a2$, $2a3$, $2a4$ and $2a5$ are formed with curve sections $2a1$-$1$ continuously disposed within the cavity $2m$ of the base body $2x$, tongue pieces $2a1$-$2$ integrally formed with the curve sections $2a1$-$1$ at the left end and the right end sections thereof, and are further formed as portions extended in the right angle direction with respect to the curved section $2a1$-$1$, and joint holes $2a1$-$3$ and $2a1$-$4$ mounted at the front and the rear portions of the tongue pieces $2a1$-$2$ at the left and the right sides thereof. Each of the joint pieces $2a1$, $2a2$, $2a3$, $2a4$ and $2a5$ has a thin section $2a1$-$5$ at the periphery of each of the joint holes $2a1$-$3$ at which each of the joint pieces $2a1$, $2a2$, $2a3$, $2a4$ and $2a5$ is overlapped with other adjacent joint pieces $2a1$, $2a2$, $2a3$, $2a4$ and $2a5$, and end ones of the joint pieces $2a1$, $2a2$, $2a3$, $2a4$ and $2a5$ are overlapped with the base body $2x$ and the front cover $2b$. The joint pieces $2a1$, $2a2$, $2a3$, $2a4$ and $2a5$ are rotatably supported by means of the pivot members 7 composed of hooks and rivets, to be inserted into the joint holes $2a1$-$3$ and $2a1$-$4$, respectively.

Figure 7:
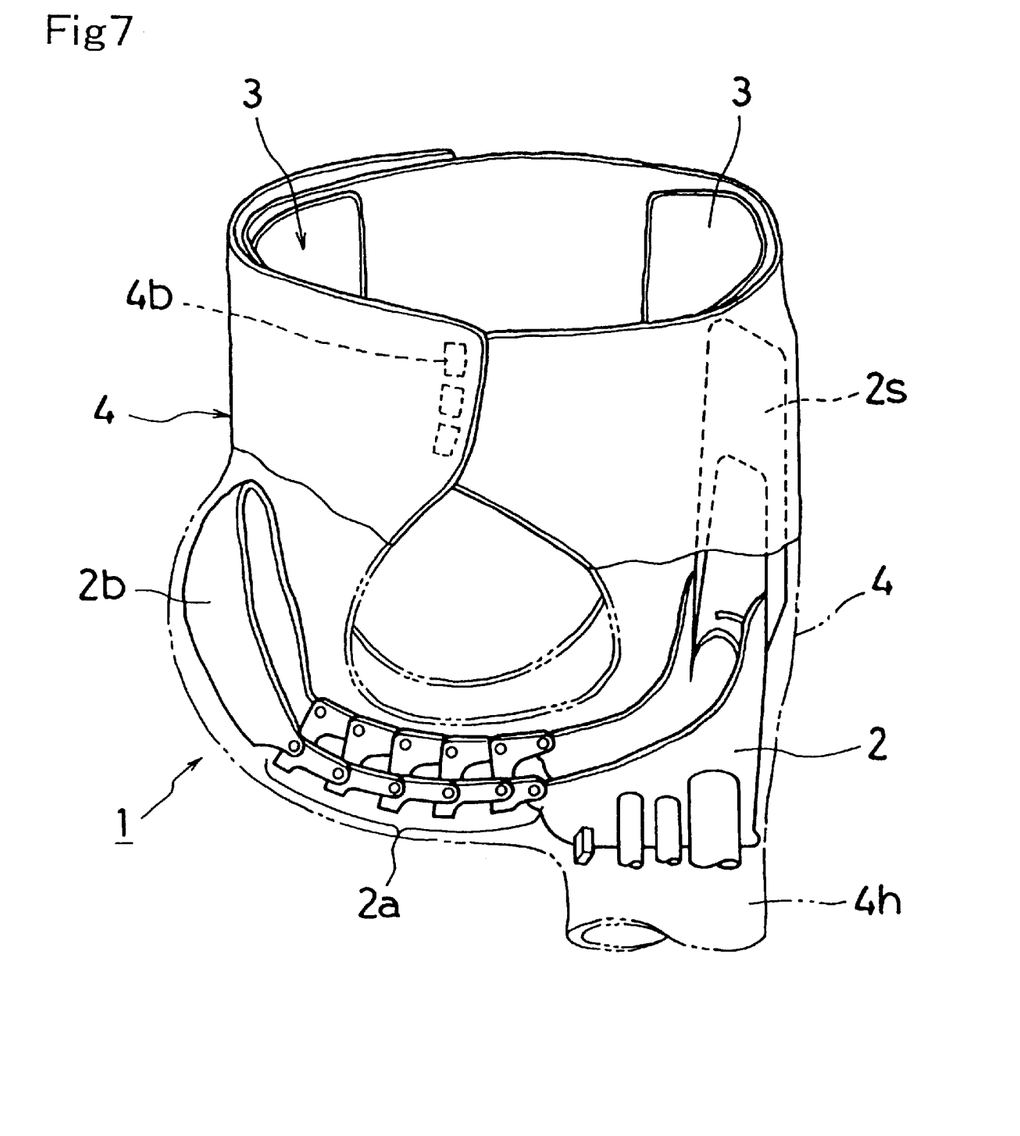
FIG. 7 is a perspective view showing a diaper cup unit 1 in the preferred embodiment of the present invention.

In the case of the L-size diaper cup body, five joint pieces $2a1$, $2a2$, $2a3$, $2a4$ and $2a5$ connected with each other are used as shown in FIGS. 2, 4, and 7. The joint piece $2a1$ is coupled with the water proof cloth $2c$ through the pivot member 7 inserted into the joint hole $2a1$-$3$ of the tongue piece $2a1$-$2$ and the joint hole $2y$ of the base body $2x$. The joint piece $2a2$ is coupled with the water proof cloth $2c$ through the pivot member 7 inserted into the joint hole $2a1$-$3$ of the joint piece $2a2$ and the joint hole $2a1$-$4$ of the joint piece $2a1$. The joint piece $2a3$ is coupled with the water proof cloth $2c$ through the pivot member 7 inserted into the joint hole $2a1$-$3$ of the joint piece $2a3$ and the joint hole $2a1$-$4$ of the joint piece $2a4$. The joint piece $2a4$ is coupled with the water proof cloth $2c$ through the pivot member 7 inserted into the joint hole $2a1$-$3$ of the joint piece $2a4$ and the joint hole $2a1$-$4$ of the joint piece $2a5$. The joint piece $2a5$ is coupled with the water proof cloth $2c$ through the pivot member 7 inserted into the joint hole $2a1$-$3$ of the joint piece $2a5$ and the joint hole $2b1$ mounted at the end portion of the front cover $2b$.

In the case of the L-size diaper cup body, five caterpillar-like joints $2a1$, $2a2$, $2a3$, $2a4$ and $2a5$ connected with each other are used as shown in FIGS. 2, 4, and 7. The L-size diaper cup body 2 has the diameter R1, as shown in FIG. 4. In this cage, the length of the bottom surface of the base body $2x$ is T, the length of the outer periphery surface of the caterpillar-like joint $2a$ is S1, and the length of the peripheral surface of the front cover $2b$ is U. The length L1 of the peripheral surface to be enveloped for the L-size diaper cup body 2 is expressed as follows.

$$L1=T+S1+U$$

Figure 5:
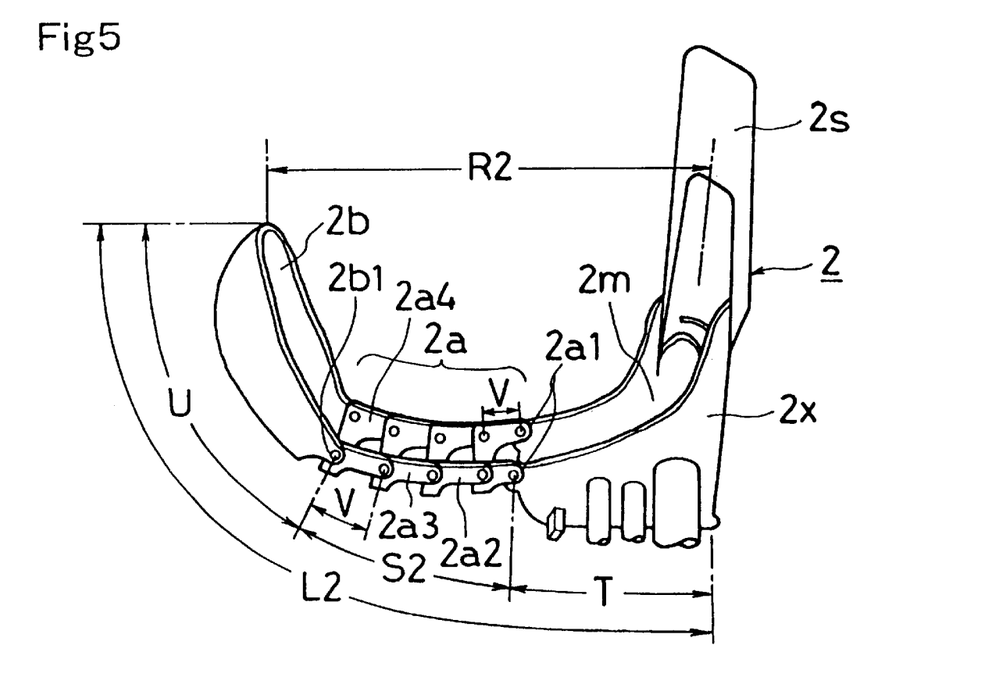
FIG. 5 is a perspective view showing an H-size diaper cup body in which a water proof cloth is removed in the preferred embodiment of the present invention.

In the case of the H-size diaper cup body 2, as shown in FIG. 5, the joint piece $2a5$, which has been used in the L-size diaper cup body, is removed from the caterpillar-like joint $2a1$, and therefore, only four joint pieces $2a1$, $2a2$, $2a3$ and $2a4$ are connected. The H-size diaper cup body 2 has the diameter R2 as shown in FIG. 5. The length of the bottom surface of the base body $2x$ is T, unchanged from the case of the L-size diaper cup body. The length of the outer peripheral surface of the caterpillar-like joint $2a$ becomes S2, which is shortened by the length V of the peripheral surface from the joint hole $2a1$-$3$ to the joint hole $2a1$-$4$ of the joint piece $2a5$. The length of the outer peripheral surface of the front cover $2b$ is U, which is unchanged from the case of the L-size diaper cup body.

The length L2 of the peripheral surface to be enveloped by the H-size diaper cup body 2 is expressed as follows:

$$L2=T+S2+U$$

The length L2 is shortened from the length L1 by the length V of the peripheral surface from the joint hole $2a1$-$3$ to the joint hole $2a1$-$4$ of the joint piece $2a5$ as follows:

$$L2=L1-V$$

Therefore, the diameter R2 of the diaper cup body 2 becomes as follows:

$$R2=R1-V$$

The diameter R2 is shortened by the length V of the peripheral surface from the joint hole $2a1$-$3$ to the joint hole $2a1$-$4$ of the joint piece $2a5$.

Figure 6:
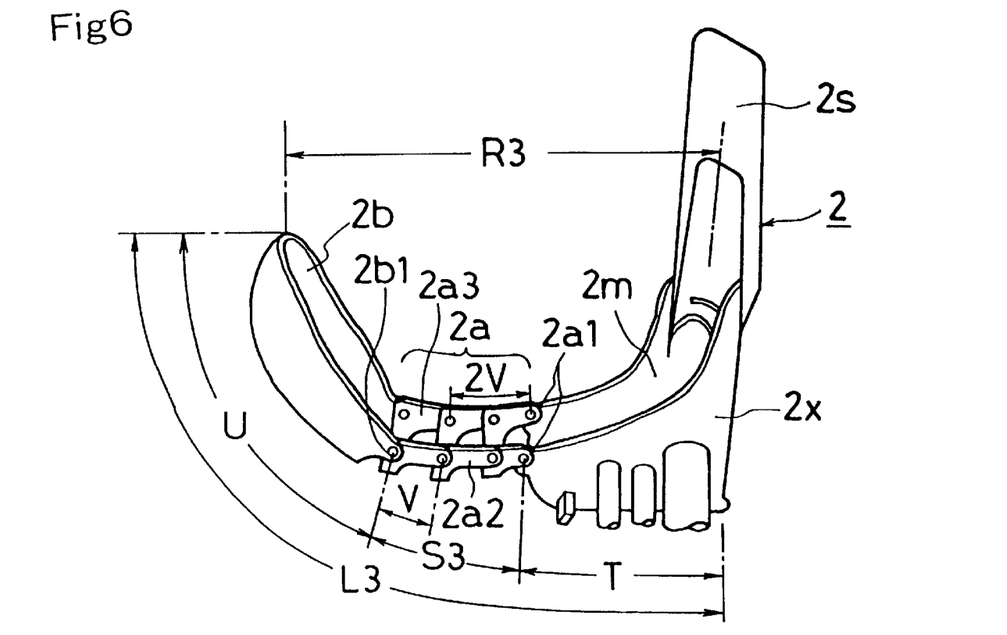
FIG. 6 is a perspective view showing an S-size diaper cup body in which a water proof cloth is removed in the preferred embodiment of the present invention.

In the case of the S-size diaper cup body 2, three joint pieces $2a1$, $2a2$ and $2a3$ are connected with each other, as shown in FIG. 6, in which two joint pieces $2a5$ and $2a4$ used in the L-size diaper cup body have been eliminated. The S-size diaper cup body 2 has the diameter R3, as shown in FIG. 6. The length of the bottom surface of the base body $2x$ is T, unchanged from the case of the H-size diaper cup body. The length of the outer peripheral surface of the caterpillar-like joint $2a$ becomes S3, which is shortened by the length 2V of the peripheral surface of two joint pieces $2a5$ and $2a4$ from the joint hole $2a1$-$3$ to the joint hole $2a1$-$4$. The length of the outer peripheral surface of the front cover $2b$ is still U, which is unchanged from the case of the L-size diaper cup body.

The length L3 of the peripheral surface to be enveloped for the S-size diaper cup body 2 is expressed as follows:

$$L3=T+S3+U$$

The length L3 is shortened from the length L1 by the length 2V of the peripheral surface of two joint pieces $2a5$ and $2a4$ from the joint hole $2a1$-$3$ to the joint hole $2a1$-$4$ as follows:

$$L3=L1-2V$$

Therefore, the diameter R3 of the diaper cup body 2 is shortened by the length 2V of the peripheral surface from the joint hole $2a1$-$3$ to the joint hole $2a1$-$4$ of two joint pieces $2a5$ and $2a4$ as follows:

$$R3=R1-2V$$

The front cover $2b$ has an approximate cup-shape, and the joint hole $2b1$ of the base end portion thereof is connected with the joint hole $2a1$-$4$ of the joint pieces $2a1$, $2a2$, $2a3$, $2a4$ and $2a5$, the number of which is adjusted in accordance with the size of the diaper cup body 2, through the pivot members 7.

As shown in FIG. 2, the water proof cloth 2c is fixed to the caterpillar-like joint 2a composed of plural joint pieces 2a1, 2a2, 2a3, 2a4 and 2a5 through the pivot members 7. The pivot members 7 are passed through the joint holes 2a1-3 and 2a1-4 of the joint pieces 2a1, 2a2, 2a3, 2a4 and 2a5 and the fastening hole 2c1 of the water proof cloth 2c for covering the caterpillar-like joint 2a, thereby rotationally supporting the joint pieces, respectively. The water proof cloth 2c is made of a fiber material, such as nylon.

A plurality of hooks 2d are used for removably attaching the spare diaper 3 and are disposed at the periphery of the cavity 2m of the diaper cup body 2, as shown in FIG. 1. The nozzle 2e for cleaning the private parts and the nozzle 2f for cleaning the anus are exclusively used for cleaning the private parts and the anus, respectively, of the patient wearing the diaper cup unit 1. The emission area of the nozzle 2e for cleaning the private parts is set wider than the emission area of the nozzle 2f for cleaning the anus. The nozzle 2e for cleaning the private parts and the nozzle 2f for cleaning the anus are disposed within the cavity 2m.

Figure 8:
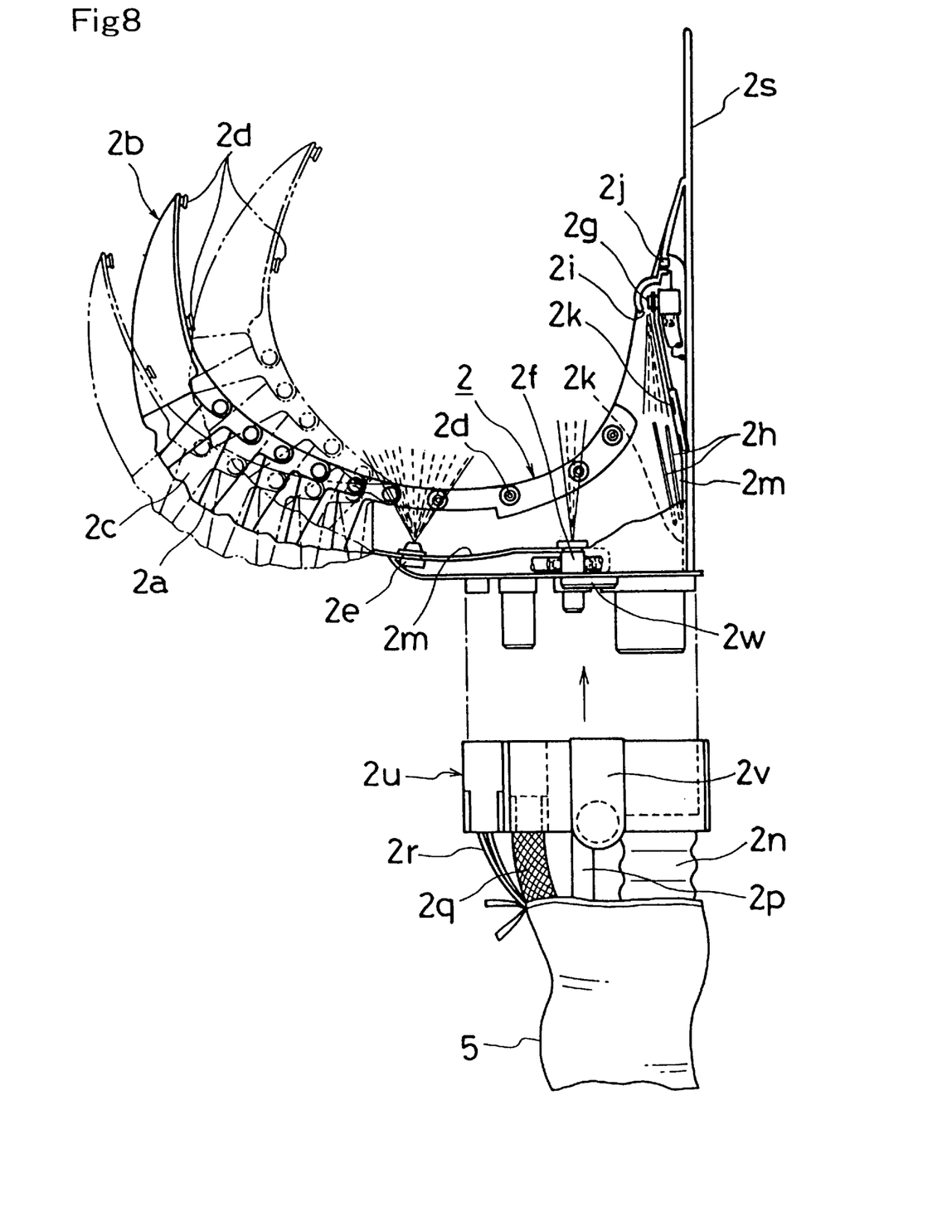
FIG. 8 is a side view showing the relationship in the connection between the diaper cup body and a hose connecting section in the preferred embodiment of the present invention.

The nozzle 2g for cleaning the cup body is used for cleaning the filth discharged by the patient or the like, and is disposed at the portion adjacent to the outlet 2i for exhausting the warm wind opened toward the side of the feces sensing sensor 2h, as shown in FIG. 8. The feces sensing sensor 2h and the urine sensing sensor 2k are used for detecting the filth discharged by the patient or the like, and are disposed at the lower side portion of the nozzle 2g for cleaning the cup body toward the filth suction hose 2n, as shown in FIG. 8.

The auxiliary outlet 2j is used for sucking the cleaning liquid or the like leaked to the upper side of the patient. The auxiliary outlet 2j is disposed at the upper portion of the diaper cup body 2 above the nozzle 2g for cleaning the diaper cup body 2, as shown in FIG. 8. Moreover, the diaper cup body 2 is connected to external devices by utilizing the filth sucking hose 2n for sucking the cleaning water and the filth within the diaper cup unit 1, the cleaning water feeding hose 2p for feeding the cleaning water into the inner side of the diaper cup body 2, the warm wind feeding hose 2q for feeding the warm wind into the inner side of the diaper cup body 2, and the sensor coupler 2r for outputting the electric signals from the feces sensing sensor 2h and the urine sensing sensor 2k, as shown in FIG. 8.

The filth sucking hose 2n is connected to the vacuum motor housing (not shown) through a filth tank (not shown) and a vacuum hose (not shown). The cleaning water feeding hose 2p is connected to a cleaning injection adjusting valve (not shown). The warm wind feeding hose 2q is connected to the vacuum motor housing (not shown). The sensor coupler 2r is connected to a sequencer (not shown) through a sensor signal line (not shown).

A waist board 2s to be contacted to the waist of the patient or the like is connected to the diaper cup body 2, as shown in FIG. 1. The waist board 2s is made of a polyethylene foam sheet with a three-layer lamination structure in which the diaper cup body 2 and a cushion material are inserted and fixed. The waist board 2s is provided with an elongated hole 2t mounted toward the warm wind feeding outlet 2i, as shown in FIG. 1.

Figure 9:
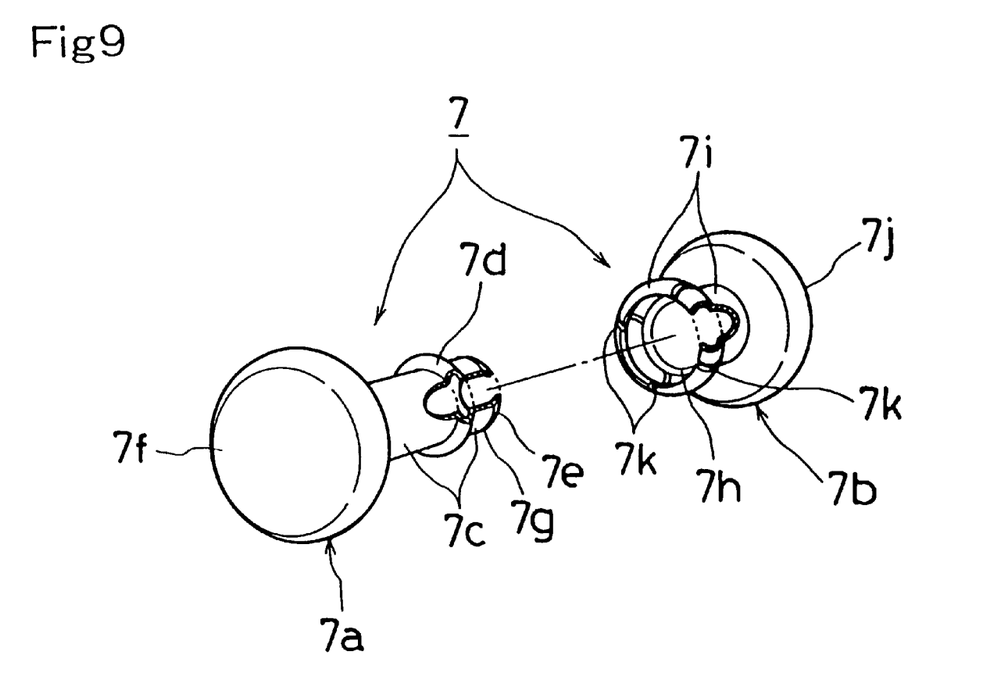
FIG. 9 is an exploded perspective view with a partial section showing pivot members in the preferred embodiment of the present invention.

With reference to FIGS. 2 and 9, a pivot member 7 will be described hereinafter.

The pivot member 7 is made of resin material or metallic material, such as stainless steel having corrosion resistance. Moreover, the pivot member 7 is similar to a removable hook composed of a rod member 7a having a cylinder section 7c and a snap member 7b having a snap hole section 7h to hold the cylinder section 7c, as shown in FIG. 9. The rod member 7a having the cylinder section 7c of the pivot member 7 is inserted into the fastening hole 2c1 of the water proof cloth 2c and the joint holes 2a1-3 and 2a1-4 of the joint pieces 2a1, 2a2, 2a3, 2a4 and 2a5, respectively, thereby coupling the rod members 7a with the snap members 7b, respectively, and whereby each of the joint pieces 2a1, 2a2, 2a3, 2a4 and 2a5 is coupled respectively. The rod members 7a and the snap members 7b also function to fix the water proof cloth 2c to the caterpillar-like joint 2a.

Moreover, in the case where it is not necessary to increase or decrease the number of the joint pieces 2a1, 2a2, 2a3, 2a4 and 2a5, the pivot member 7 can be replaced with a rivet made of resin to be caulked by using heat, or a metallic rivet with corrosion resistance to be caulked by using pressure.

The pivot member 7a is formed with a cylinder section 7c having a beveled section 7e and a projection 7d at one end thereof, and a head section 7f formed at the other end of the cylinder section 7c. The snap member 7b is formed with a snap hole section 7h to be fitted with the projection 7d of the rod member 7a at one end thereof, and a cylinder section 7i to be fitted with the end point of the cylinder section 7c. The cylinder section 7c is formed as a thin metallic tube or a resin tube to provide resilient property for the projection 7d. The snap hole section 7h has a plurality of slits 7k at the periphery thereof to provide resilient property for the snap hole section 7h.

Next, a spare diaper 3 will be described hereinafter. As shown in FIG. 1, the spare diaper 3 is provided with an elongated hole 3e at the central portion thereof for being inserted into the connecting section 2u, such as a hose, frills 3a disposed at the left and right sides of the elongated hole 3e for avoiding any leakage in the lateral direction, hooks 3b disposed at the diaper side corresponding to the hooks disposed at the cup body side 2d, respectively, and magic tapes (e.g., adhesive tapes or hook and pile fastener strips) 3c to be coupled with corresponding magic tapes 4a disposed on the diaper cover 4, a bag 3d for receiving the waist board 2s, and a waist cover 3k to be attached to the waist of the patient or the like.

Moreover, the spare diaper 3 is attached to the inside portion of the diaper cup body 2 by coupling the hooks 2d and the hooks 3b to be applied to the waist and hips of the patient or the like. Thus, the spare diaper 3 is disposed at the periphery of the cavity 2m of the diaper cup body 2, and the spare diaper 3 is composed of a cover section 3f for covering the waist and hips of the patient or the like, and fastening belt sections 3g and 3h for winding the waist of the patient or the like. The spare diaper 3 is formed with cloth made of a nylon material with, for example, an approximately T-letter shape as a whole.

The frills 3a for avoiding leakage in the lateral direction are disposed at both sides of the elongated hole 3e at the inside of the spare diaper 3. The frills 3a for avoiding leakage in the lateral direction are formed with cloth made of a nylon material, for example, having water proof properties, and sewed on the spare diaper 3 so that the frill can be elastic. Each of the hooks 3b is fixed at each of the holes disposed at the periphery of the elongated hole 3e of the spare diaper 3, respectively, by fitting a front member to a rear member with pressure. The hooks 3b are disposed within the inside portion of the spare diaper 3 so that the hooks 3b are hidden by the frills 3a used for avoiding leakage in the lateral direction. The length of each of the magic tapes 3c, 3i, and 3j is lengthened so that the position to be coupled with each of the magic tapes can be adjustable to fit, even in the case where the size of the diaper cup body 2 is changed in accordance with the size of the waist and hips of the person to whom the spare diaper 3 is applied.

The fastening belt sections 3g and 3h are provided with the magic tapes 3i and 3j at the corresponding left and right positions, respectively, thereby performing the function of the belt for attaching the diaper cup body 2 to the waist and hips of the patient or the like. The length of each of the magic tapes 3i and 3j mounted on the fastening belt sections 3g and 3h, respectively, is lengthened in the direction for winding it around the waist and hips portion so that the fastening belt sections 3g and 3h can be wound suitably regardless of the size of the waist and hips of the human body. The spare diaper 3 is formed with an outside cloth (not shown), an inside cloth (not shown), and a mesh cloth (not shown) sandwiched between the outside cloth and the inside cloth for easily absorbing moisture. The mesh cloth is, for example, a cloth made of nylon material with increased space therein, thereby increasing the water absorbing property. The outside cloth and the inside cloth are woven tightly in comparison with the mesh cloth.

Next, the diaper cover 4 will be described hereinafter.

As shown in FIGS. 1 and 7, the diaper cover 4 is provided with magic tapes 4a, 4b, 4c, 4d, 4e, 4i and 4j, a fastener 4f, a hose unit passing hole 4g, and a hose unit cover section 4h.

The diaper cover 4 is formed in the shape of an approximate T-letter similar to the spare diaper 3. The diaper cover 4 is a member made of cloth which is composed of a waist and hips covering section 4k for covering the cover section 3f, and a belt section 4m and 4n in the shape of an approximate T-letter for covering the fastening belt sections 3g and 3h. The diaper cover 4 has a cut section 4p for dividing the portion from the hose unit cover section 4h to the outside of the diaper cover 4 through the hose unit passing hole 4g. The fastener 4f is disposed at the cut section 4p so as to be opened.

The diaper cover 4 can be attached with the spare diaper 3 by coupling the magic tapes 4a with the magic tapes 3c of the spare diaper 3, respectively. The diaper cover 4 per se can be fixed to a human body by coupling the magic tapes 4a, 4b, 4c, 4d, 4e, 4i and 4j with a cloth made of French pile of the diaper cover 4, respectively. If the length in the winding direction of the magic tapes 4i and 4j mounted on the belt section 4m and 4n is lengthened, the diaper cover 4 can be suitably fit to the waist and hips of the human body without regard to the size of the waist and hips. By using the fastener 4f, it is possible to remove only the diaper cover 4 by opening the fastener 4f, even when the connecting section 2u for hoses is connected to the diaper cup body 2.

The waist and hips covering section 4k divides the portion from the hose unit covering section 4h at the lower side of the hose unit passing hole 4g to the upper end thereof, and can be opened by opening the fastener 4f mounted on the covering section 4k. The hose unit passing hole 4g shown in FIG. 1 is an elongated hole extended along the central line of the diaper cover 4 and is conformed with the connecting section 2u for a hose or the like.

The hose unit covering section 4h is a cylindrical body jointed to the hose unit passing hole 4g to hide the connecting section 2u for a hose or the like. The cylindrical hose unit covering section 4h can be opened by opening the fastener 4f, since the fastener 4f is disposed at the front and central portion and in the longitudinal direction, as shown in FIG. 1.

At the upper side of the rear surface of the diaper cover 4, there is provided a resilient rubber portion (not shown) that fits the upper peripheral portion of the diaper cover 4 to the waist portion of the human body. Moreover, there is provided a waist pad 4r as a cushion member at an approximately central portion of the rear surface of the diaper cover 4.

As mentioned above, the diaper cup body 2, the spare diaper 3, and the diaper cover 4 are jointed with each other by coupling the spare diaper 3 with the diaper cup body 2 by using the hooks 2d and 3b. The spare diaper 3 is then coupled with the diaper cover 4 by using the magic tapes 3c, 3i, 3j, 4a, 4b, 4c, 4e, 4i and 4j. Thus diaper cup unit 1 shown in FIG. 7 is completed.

As shown in FIG. 8, the diaper cup unit 1 is connected with the connecting section 2u for hoses or the like. The connecting section 2u is used for connecting the diaper cup unit 1 and external devices, and is integrally composed of the filth sucking hose 2n, the cleaning water feeding hose 2p, the warm wind feeding hose 2q and the sensor coupler 2r1. The connecting section 2u supports these components integrally. The connecting section 2u is removable from the diaper cup body 2, and the hold piece 2v is fixed to the cramp 2w mounted on the side of the diaper cup body 2. A hose cover 5 is mounted so as to cover the hose unit covering section 4h of the diaper cover 4.

The operation of the preferred embodiment according to the present invention will be described hereinafter.

In the case where the diaper cup unit 1 is used for a person whose waist and hips size is L1, the caterpillar-like joint 2a having five joint pieces 2a1, 2a2, 2a3, 2a4, and 2a5 is used, as shown in FIG. 4. The spare diaper 3 can be attached to the waist and hips of a human body by adjusting the positions of the fastening belt sections 3g and 3h corresponding to the magic tapes 3i and 3j, respectively, without regard to the size of the waist and hips of the human body. The diaper cover 4 can be attached to the waist and hips without regard to the size of the waist and hips of the human body by lengthening the length of the magic tapes 4i and 4j mounted on the belt sections 4m and 4n in the winding direction around the waist and hips.

In the case where the diaper cup unit 1 is used for a person whose waist and hips size is H, one of the joint pieces, i.e., the joint piece 2a5, is removed from the L-size diaper cup unit 1, as shown in FIG. 5. The joint piece 2a5 is removed by removing the rod member 7a and the snap member 7b of the pivot member 7 which have been used for jointing the joint piece 2a5 between the front cover 2b and the joint piece 2a4. Therefore, four joint pieces 2a1, 2a2, 2a3, and 2a4 of the caterpillar-like joint 2a are connected together for use in the diaper cup unit 1. By this, the length of the outer peripheral surface of the caterpillar-like joint 2a of the H-size diaper cup body 2 is shortened by the length V from the joint hole 2a1-3 to the joint hole 2a1-4 of the joint piece 2a5, thereby becoming S2. Therefore, the diaper cup unit 1 can be fitted to the H-size human body.

In the case where the diaper cup unit 1 is used for a person whose waist and hips size is S, two of the joint pieces, i.e., the joint pieces 2a5 and 2a4, are removed from the L-size diaper cup unit 1, as shown in FIG. 6. The joint pieces 2a5 and 2a4 are removed by removing the rod members 7a and the snap members 7b of the pivot member 7 which have been used for jointing the joint pieces 2a5 and 2a4 between the front cover 2b and the joint piece 2a3. Therefore, three joint pieces 2a1, 2a2 and 2a3 of the caterpillar-like joint 2a are connected together for use in the diaper cup unit 1. By this, the length of the outer peripheral surface of the caterpillar-like joint 2a of the S-size diaper cup body 2 is shortened by the length 2V from the joint holes 2a1-3 to the joint holes 2a1-4 of the joint pieces 2a5 and 2a4, thereby becoming S3. Therefore, the diaper cup unit 1 can be fitted to the S-size human body. Thus, the diaper cup unit 1 can be changed to a desired size easily by adjusting the number of the joint pieces 2a1, 2a2, 2a3, 2a4 and 2a5.

The present invention is constructed as described above. As a result, the following features and effects are obtained.

The present invention is a diaper used for a discharge disposing apparatus provided with a diaper cup body enveloping the waist and hips of a human body, a cleaning water feeding hose connected to the diaper cup body for feeding water into the inside of the diaper cup body, and a filth sucking hose connected to the diaper cup body for sucking the cleaning water and the filth within the inside of the diaper cup body. The diaper cup body is composed of a base body provided with the cleaning water feeding hose and the filth sucking hose, a caterpillar-like joint rotatably coupled with the base body, and a front cover rotatably coupled with the caterpillar-like joint. The caterpillar-like joint is connected with a plurality of joint pieces, and the size of the diaper cup body is adjustable by increasing or decreasing the number of the joint pieces. Therefore, it is possible to utilize the diaper cup body with appropriate adjustments without regard to the size of the human body from adult to child, to wind and fit the caterpillar-like joint around the periphery of the waist and hips of the human body, and to avoid any leakage of cleaning water from the portions of the caterpillar-like joint.

The joint pieces of the diaper cup body are integrally formed with curve sections, tongue pieces are formed at both sides of the curve sections, and joint holes are provided at the front and the rear portions of each of the tongue pieces. Therefore, a plurality of joint pieces are connected easily.

The joint pieces are formed with thin sections at the periphery of the joint holes mounted on the tongue pieces Therefore, it is possible to rotate the joint pieces smoothly, and to remove the irregularity of the jointed portions between the joint pieces.

The joint holes of the joint pieces are connected to each other by removable pivot members. Therefore, it is possible to increase or decrease the number of the joint pieces easily, thereby changing the size of the diaper cup body easily and attaching it without regard to the size of the human body on which it is attached.

The pivot members are passed through the joint holes of the joint pieces and fastening holes mounted on a water proof cloth to fasten the water proof cloth to the joint pieces for covering the caterpillar-like joint with the water proof cloth. Therefore, it is possible to couple the joint piece with the water proof cloth by using the pivot members as a common member, and to reduce the number of fabrication parts and processes, thereby reducing the fabrication cost.

The pivot members are composed of a rod member and a snap member, the rod member is formed with a head section at one end thereof and a projection section at the other end thereof to form a cylinder section, and the snap member is formed with a head section at one end thereof and a projection section at the other end thereof to form a snap hole section. Therefore, it is possible to utilize the pivot member removably, thereby achieving the changes of the number of joint pieces and of the size of the diaper cup body.

It will be appreciated that the present invention is not limited to the exact construction that has been described above and illustrated in the accompanying drawings, and that various modifications and changes can be made without departing from the scope and spirit thereof. It is intended that the scope of the invention only be limited by the appended claims.

What is claimed is:

1. A discharge disposing apparatus, comprising:

a diaper cup body adapted to envelope the waist and hips of a human body;

a cleaning water feeding hose connected to the diaper cup body for feeding water into the inside of the diaper cup body; and a filth sucking hose connected to the diaper cup body for sucking cleaning water and filth from within the inside of the diaper cup body;

wherein the diaper cup body is composed of a base body provided with the cleaning water feeding hose and the filth sucking hose, a caterpillar-like joint rotatably coupled with the base body, and a front cover rotatably coupled with the caterpillar-like joint, the caterpillar-like joint is connected with a plurality of joint pieces, and the size of the diaper cup body is adjustable by increasing or decreasing the number of the joint pieces; and wherein the joint pieces are integrally formed with curve sections, tongue pieces formed at both sides of the curve sections, and joint holes mounted at the front and the rear portions of each of the tongue pieces.

2. The discharge disposing apparatus according to claim 1, wherein the joint pieces are formed with thin sections at the periphery of the joint holes mounted on the tongue pieces.

3. The discharge disposing apparatus according to claim 2, wherein the joint holes of the joint pieces are connected with each other by removable pivot members.

4. The discharge disposing apparatus according to claim 3, wherein the pivot members are passed through the joint holes of the joint pieces and fastening holes mounted on a water proof cloth to fasten the water proof cloth to the joint pieces for covering the caterpillar-like joint with the water proof cloth.

5. The discharge disposing apparatus according to claim 4, wherein the pivot members are each composed of a rod member and a snap member, the rod member is formed with a head section at one end thereof and a projection section at the other end thereof to form a cylinder section, and the snap member is formed with a head section at one end thereof and a snap hole section at the other end thereof to be coupled to the projection section.

6. The discharge disposing apparatus according to claim 1, wherein the joint holes of the joint pieces are connected with each other by removable pivot members.

7. The discharge disposing apparatus according to claim 6, wherein the pivot members are passed through the joint holes of the joint pieces and fastening holes mounted on a water proof cloth to fasten the water proof cloth to the joint pieces for covering the caterpillar-like joint with the water proof cloth.

8. The discharge disposing apparatus according to claim 7, wherein the pivot members are each composed of a rod member and a snap member, the rod member is formed with a head section at one end thereof and a projection section at the other end thereof to form a cylinder section, and the snap member is formed with a head section at one end thereof and a snap hole section at the other end thereof to be coupled to the projection section.

9. A discharge disposing apparatus, comprising:

a diaper cup body adapted to envelope the waist and hips of a human body;

a cleaning water feeding hose connected to the diaper cup body for feeding water into the inside of the diaper cup body;

a filth sucking hose connected to the diaper cup body for sucking cleaning water and filth from within the inside of the diaper cup body; and said diaper cup body is composed of a base body provided with the cleaning water feeding hose and the filth sucking hose, a flexible joint portion rotatably coupled with said base body, and a front cover rotatably coupled with the flexible joint portion, the flexible joint portion comprises a plurality of curved joint pieces removably connected together between said base body and said front cover, and the size of said diaper cup body is adjustable by removing said joint pieces from or adding additional joint pieces to said flexible joint portion;

wherein the joint pieces are integrally formed with curve sections and tongue pieces formed at both sides of the curve sections, and joint holes are mounted at front and rear portions of each of the tongue pieces.

10. The discharge disposing apparatus according to claim 9, wherein the joint holes of the joint pieces are connected with each other by removable pivot members.

11. The discharge disposing apparatus according to claim 10, wherein the pivot members are passed through the joint holes of the joint pieces and fastening holes mounted on a water proof cloth to fasten the water proof cloth to the joint pieces for covering the flexible joint portion with the water proof cloth.

12. The discharge disposing apparatus according to claim 11, wherein the pivot members are each composed of a rod member and a snap member, the rod member is formed with a head section at one end thereof and a projection section at the other end thereof to form a cylinder section, and the snap member is formed with a head section at one end thereof and a snap hole section at the other end thereof to be coupled to the projection section.

* * * * *

UNITED STATES PATENT AND TRADEMARK OFFICE
CERTIFICATE OF CORRECTION

PATENT NO.   : 6,394,988 B1
DATED        : May 28, 2002
INVENTOR(S)  : Takeo Hashimoto It is certified that error appears in the above-identified patent and that said Letters Patent is hereby corrected as shown below:

Title page,
Item [73], Assignee, should read -- Niles Parts Co., LTD., Tokyo (JP) --

Signed and Sealed this

Seventh Day of June, 2005

JON W. DUDAS
*Director of the United States Patent and Trademark Office*